United States Patent [19]

Willert

[11] Patent Number: 4,715,236

[45] Date of Patent: Dec. 29, 1987

[54] POWER TRANSFORMER INSPECTION PROCEDURE

[75] Inventor: Thomas E. Willert, Bellingham, Wash.

[73] Assignee: Puget Sound Power and Light Company, Bellevue, Wash.

[21] Appl. No.: 914,883

[22] Filed: Oct. 3, 1986

[51] Int. Cl.[4] ............................................. G01N 1/00
[52] U.S. Cl. .................................................. 73/863.86
[58] Field of Search ............... 73/863, 863.81, 863.82, 73/863.85, 863.86, 864, 864.31, 864.33, 864.51, 864.73, 864.74, 863.86; 208/262; 210/909; 137/317, 318

[56] References Cited

U.S. PATENT DOCUMENTS

| | | | |
|---|---|---|---|
| 1,795,430 | 3/1931 | Howie et al. | 137/318 |
| 3,068,724 | 12/1962 | Mueller | 137/318 |
| 3,992,155 | 11/1976 | Nilsson | 73/864.34 |
| 4,046,013 | 9/1977 | Green | 73/863.81 |
| 4,058,373 | 11/1977 | Kurz et al. | 73/19 |
| 4,350,052 | 9/1982 | Kendall | 73/863.86 |
| 4,430,208 | 2/1984 | Pytewski et al. | 210/909 |
| 4,578,194 | 3/1986 | Reinartz et al. | 210/909 |

OTHER PUBLICATIONS

*Chicago Specialty Manufacturing Company,* Catalog No. 26–76, 1976/77, p. 47.

*Primary Examiner*—Stewart J. Levy
*Assistant Examiner*—Robert R. Raejis
*Attorney, Agent, or Firm*—Seed and Berry

[57] ABSTRACT

A method for sampling oil from operating electrical distribution transformers includes the steps of determining the thickness of the container, forming a bore partially through the container wall, placing a self-tapping screw in the bore, and advancing the plug to penetrate the inner surface of the wall. The screw includes means for sealing the bore after the inner wall surface has been penetrated. The screw is counter-rotated to allow dielectric fluid to exit the bore in a controlled manner. The screw is then re-rotated to seal the bore. Samples may be obtained without removing the transformer from service.

5 Claims, 5 Drawing Figures

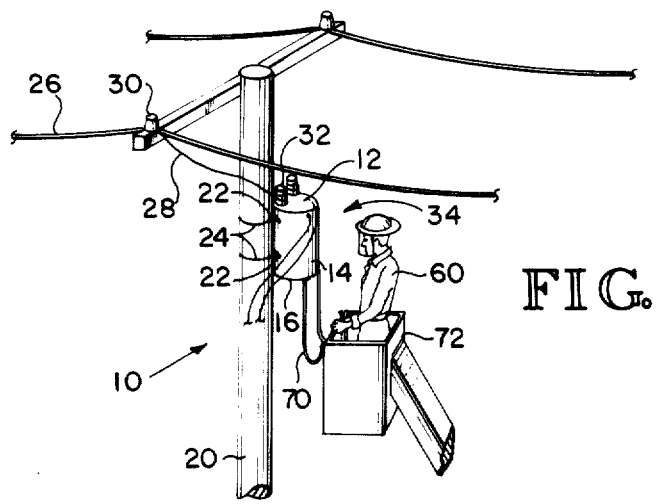
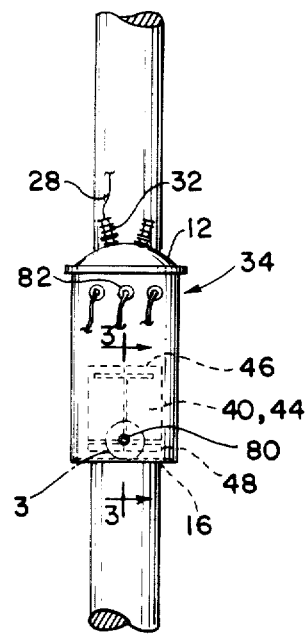
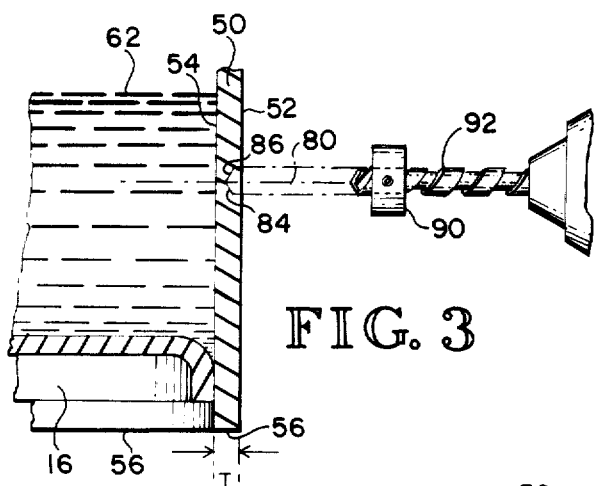
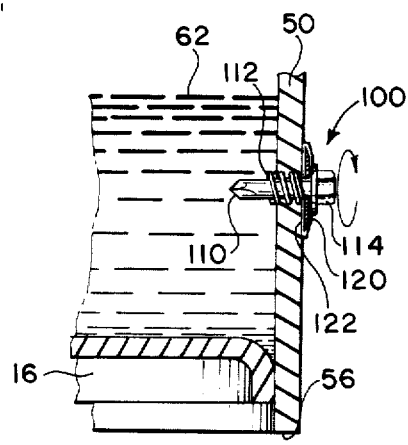

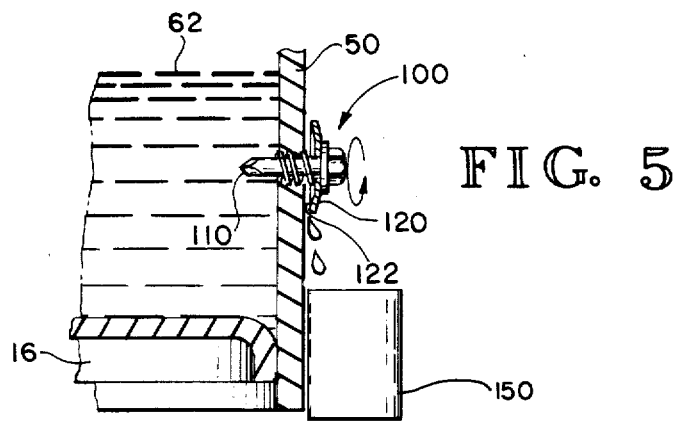

POWER TRANSFORMER INSPECTION PROCEDURE

DESCRIPTION

TECHNICAL FIELD

The invention relates to a method for obtaining fluid samples from a sealed vessel. More specifically, the invention relates to a method for safely obtaining samples of dielectric oil from electrical power transformers.

BACKGROUND ART

It has recently become known that polychlorinated biphenyl products (PCBs) may be hazardous to human health. In the past, PCBs were commonly used as a fire-retardant material in dielectric oil used for cooling and insulating electrical distribution transformers.

Electric utilities have been required to identify distribution transformers containing PCBs as part of an effort to eliminate these chemicals from the environment. Therefore, it has become necessary to obtain fluid samples from a large number of electrical distribution transformers.

One common electrical distribution transformer is the overhead distribution transformer, commonly referred to as a "bug." This type of distribution transformer is designed to be mounted on poles at substantial heights above the ground. Such transformers may be mounted singly for single-phase services or in groups called "banks" for three-phase services. These transformers typically range in capacity from 5 kVA to 167 kVA. Transformers of this type usually include a substantially can-shaped container which is covered by a lid and sealed with a gasket between the container and lid.

The container houses the primary and secondary windings of the transformer, which are wound about a transformer core. The coils and core are typically completely immersed in an oil having a high dielectric constant to insulate the primary and secondary windings from one another. Heat generated by the windings and core during the operation of the transformer is transferred through the oil to the container and dissipated in the surrounding air.

Presently, oil samples are obtained by removing the top of the transformer from the container, retrieving an oil sample, and replacing the lid. This procedure requires that the transformer be removed from electrical sevice so that the workmen can safely work inside of the container. When removing and replacing the lid, some of the fluid inevitably drips from the lid onto the ground. Because all unidentified transformers are treated as if they are PCB-contaminated, these spills must be cleaned up in compliance with rules promulgated by the Environmental Protection Agency. Steps which must be taken include digging up ground which has been contaminated with oil, disposing of all clothing which has become contaminated with oil, and cleaning tools, etc., which may have become contaminated.

Typically, only about ten distribution transformers of the above-described type can be sampled in a working day using a three-person work crew. A significant disadvantage of this technique is that workers are directly exposed to oil which may be contaminated. Furthermore, the transformer must be removed from service (i.e., electrical power disrupted to customers) while the transformer is being sampled. In addition, the gasket between the lid and container must be replaced. It has also been found that removing the lid of the transformer exposes the dielectric fluid to possible contamination. Testing of the transformer is often limited to periods when it is not raining or snowing.

Therefore, a need exists for a method of obtaining oil samples from distribution transformers which eliminates the disadvantages of the prior art technique.

DISCLOSURE OF THE INVENTION

It is an object of the invention to provide a quick and easy method of safely sampling oil in electrical distribution transformers, thereby reducing the cost of inspecting such transformers.

It is an object of the invention to obtain a fluid sample from an electrical distribution transformer without interrupting electrical service from the transformer.

It is also an object of the invention to obtain a fluid sample from an electrical distribution transformer while minimizing the potential of spilling any such fluid.

It is yet another object of the invention to obtain a fluid sample from an electrical distribution transformer while minimizing exposure of workers to oil which may be contaminated.

The invention achieves these and other objects, which will become apparent from the description which follows, by utilizing a self-tapping device which is driven through a bore which has been partially formed through a wall of the transformer.

In the preferred embodiment, a position is located near the bottom of the transformer for forming the bore. The located position is beneath the primary and secondary coils of the transformer so that inadvertent contact with the windings is prevented during subsequent boring and device-driving steps. After the desired position has been located, a bore is formed, preferably by drilling, at the located position. The bore extends only partially through the wall of the transformer so that a reduced thickness wall portion remains adjacent to an inner wall surface of the transformer.

In the preferred embodiment, a self-tapping screw, having a drilling end, a threaded midsection, and a driving end, is then positioned in the bore. The screw-driving end is rotated to advance the drilling end through the reduced thickness wall portion so as to penetrate the inner wall surface. The self-tapping screw has a seal, which seals the bore after the drilling end of the screw has penetrated the inner wall surface. The screwdriving end is preferably rotated at a speed which is sufficient to prevent any substantial loss of the fluid from the bore. The screwdriving end may then be counterrotated to unseal the bore and allow fluid to exit therefrom for accumulation in a sample bottle. The screwdriving end is then re-rotated to reseal the bore. Any fluid remaining outside the bore can be removed with a cloth saturated in denatured alcohol.

Oil drips can be collected by attaching a sheet of plastic or other suitable material to the base of the transformer, beneath the bore location, and the basket of a lift truck. The cloth or sheet should then be discarded according to Environmental Protection Agency regulations. Workers should also wear protective clothing, including gloves, protective garments, and face protection, in the event that hot oil is ejected from the bore when the drilling end of the screw penetrates the container inner wall surface.

BRIEF DESCRIPTION OF THE DRAWINGS

FIG. 1 is an isometric view of a conventional distribution transformer in service on a utility pole. A worker in shown in the basket of a lift truck with a protective sheet secured to the transformer and the basket of the lift truck.

FIG. 2 is an enlarged elevational view of the distribution transformer shown in FIG. 1, with the positions of the windings and secondary bushings indicated by dashed lines.

FIG. 3 is an enlarged sectional view of circled area 3 in FIG. 2, taken along the line 3—3, showing a bore formed after a bore-forming step.

FIG. 4 is an enlarged sectional veiw, similar to FIG. 3, showing a self-tapping screw inserted through the bore in a sealing position.

FIG. 5 is an enlarged sectional veiw, similar to FIGS. 3 and 4, showing the self-tapping screw in an unsealing position, with fluid exiting the bore.

BEST MODE FOR CARRYING OUT THE INVENTION

The present invention is directed towards a method for sampling dielectric fluid in electrical distribution transformers. Before describing the details of the method of the present invention, it will helpful to consider the construction and position of various components in conventional electrical distribution transformers. Although the method of the present invention is described for use in a particular type of electrical transformer, it is to be understood that the method has wide application for sampling fluid contained in other varieties of electrical distribution transformers when the fluids may be contaminated and it is desirable to prevent leakage or spillage of the fluid.

A conventional electrical distribution transformer, generally indicated at reference numeral 10, is shown in FIG. 1. The transformer has a lid 12 which covers a generally cylindrical steel container 14 having a bottom 16. The transformer is mounted on a utility pole 20 by hangers 22 and metal straps 24. Grid voltage is delivered to the transformer by an overhead line 26 and a cable 28, which are supported at the top of the utility pole by an insulator 30. A primary bushing 32 on the lid 12 delivers the grid power to the inside of the transformer. Secondary bushings, generally indicated at reference numeral 34, deliver step-down voltage to the consumer.

As shown in FIG. 2, the primary bushing 32 is electrically connected to a primary winding 40 which is adjacent to a secondary winding 44. The windings are wrapped about a core 46 which increases magnetic coupling between the coils. The base 48 of the core rests on the bottom 16 of the transformer. The core 46 is typically positioned so that the base 48 is in a plane which is generally spaced from a plane which is loosely defined by the secondary bushings 34.

As shown in the remaining figures, the generally cylindrical steel container 14 has a continuous wall 50 defined by an outer wall surface 52 and an inner wall surface 54. The bottom 16 is typically joined to the inner wall surface 54, such as by welding, such that the thickness T of the continuous wall 50 is discernible by inspection of the lower edge 56 thereof. The thickness T of the continuous wall may also be determined by the thickness of the hangers 22, which are usually made from the same sheet metal stock.

The preferred method of performing the present invention minimizes exposure of a lineman 60 to dielectric fluid 62 contained within the transformer 10 while obtaining a sample of the fluid. The present method does not require that power to the transformer be disconnected while the sample is obtained.

Throughout the procedure described below, any transformer which has not been identified as having a concentration of PCBs below a predetermined level should be treated as if it is PCB-contaminated. Therefore, as shown in FIG. 1, polyethylene sheeting 70 should be suspended below the work area between the transformer bottom 16 and the basket 72 in which the worker is located. Any suitable means, such as clothespins, may be used to connect the polyethylene sheeting to the transformer and basket to form a catch basin for fluid drips. As shown in FIGS. 2 and 3, a position 80 is located beneath a secondary neutral bushing 82 approximately two inches up from the lower edge 56 of the continuous wall 50.

It is an object of the next step of the method to form a bore 84 part of the way through the continuous wall 50 at the located position 80 so as to leave a reduced thickness wall portion 86 adjacent to the inner wall surface 54. In the embodiment shown, the preferred depth of the bore 84 is almost three-fourths of the thickness of wall 50. An adjustable drill bit collar 90 is positioned on a hardened steel drill bit 92 so that the exposed drill end is approximately equal to the desired depth of the bore, according to the measured thickness T of the continuous wall 50. The located position 80 is preferably marked with a conventional punch to guide the drill bit 92. In order to prevent the collar 90 from slipping on the drill bit 92 without warning, it is preferable to drill the bore 84 at a relatively slow rate, such as between 100-300 rpm so that slippage of the collar can be observed and preferably avoided. If the inner wall surface 54 is prematurely punctured during the bore-forming step, the bore may be quickly plugged with a wooden plug, such as a golf tee, until the next step can be performed.

It is important to note that the located position 80 substantially reduces the possibility that a drill bit or other object may penetrate through the inner wall surface 54 and contact either the windings 40, 44 or another current-carrying conductor in the transformer. At this location, the base 48 of the core 46, which should not be carrying any current, is the closest structure. Furthermore, the base is well behind the continuous wall 50 at this location.

After the bore 84 has been formed, a self-tapping screw, generally indicated at reference numeral 100, is inserted into the bore. The plug has a drilling end 110, a threaded midsection 112, and a driving end 114. The preferred self-tapping screw is a no. 12 by ¾ inch hex TEK (self-tapping washer head stainless steel screw) available from Allied Bolt in Seattle, Washington. The threaded midsection 112 of the screw preferably has a constant diameter of approximately 0.216 inch. When this size screw is used, it it preferred that the bore 84 be drilled with an 11/64 drill bit having a diameter of approximately 0.172 inch. Thus, the diameter of the bore is slightly smaller than the diameter of the threaded midsection to assure that the threads achieve a good bite in the bore. As stated above, it is preferred to use a self-tapping screw having a substantially constant threaded midsection. It has been found that the use of conventional self-tapping repair plugs, which typically have a threaded midsection of increasing diameter, may not permanently seal the bore. The self-tapping screw 100 also has a no. 12 by ⅜ inch Belleville-style neobond washer 120, available from Allied Bolt in Seattle, Washington, which seals the bore. The washer preferably has a neoprene (polychloroprene) coating (approximately 1/16 inch thick) which serves as an oil—resistant seal for the bore. The screw-drilling end 110 and midsection 112 have a preferred combined length which is only slightly greater than the thickness T of the continuous wall 50 so that the washer 120 immediately seals the bore after the inner wall surface 54 is punctured by the drilling end 110.

The self-tapping screw 100 is driven into the bore at a preferred rate of approximately 100-300 rpm until the drilling end 110 pierces the inner wall surface 54 and the washer 120 seats against the outer wall surface 52 to seal the bore 84. A battery-operated electric drill will suitably drive the screw at the above rate. It has been found that by driving the screw at this rate, minimal leakage of dielectric fluid is experienced from the bore after the inner wall surface has been punctured. It is highly desirable for the worker operating the dril to wear protective gloves and clothing, including a face shield, to assure that the worker is portected from oil which may be ejected through the bore during the driving step due to pressurization of the oil from elevated operating temperatures inside the transformer 10.

After the self-tapping screw 100 has been driven through the bore such that the inner wall surface 54 is pierced and the bore sealed, the worker may then counterrotate the screw, as shown in FIG. 5, using a conventional wrench (not shown) to allow dielectric fluid 62 in the transformer 10 to exit the bore at a controlled rate for collection in a sample bottle 150 FIG. 5). Once the sample has been taken, the self-tapping screw 100 sould be retightened, and any excess dielectric fluid on the outside of the transformer removed with a cloth saturated with denatured alcohol. Chlorinated solvents should not be used.

In order to insure the integrity and permanence of the seal at the bore, a Belleville-style washer 120, described above, is preferably used. The Belleville-style washer maintains an outward axial force on the driving end 114 of the self-tapping screw 100 when the screw is tightened. This axial force resists counterrotation of the screw due to thermal expansion and contraction of the continuous wall 50 during transformer operation. The neoprene coating 122 on the washer 120 is an oil-resistant material which serves as an elastomeric gasket that insures that a good seal will be maintained. It is also preferred to coat the junctions between the outer wall surface 52, washer 120, and driving end 114 of the self-tapping screw 100 with an epoxy-based coating or galvanized zinc paint in order to discourage counterrotation of the screw 100. These epoxy-based coatings are commercially available in a spray can. The junctions should only be coated after the surfaces have been appropriately cleaned as described above.

The method of the present invention, as described above, provides a safe and convenient method for obtaining dielectric fluid samples from electrical distribution transformers. The described method drastically reduces exposure of workers to dielectric fluid which may be contaminated with PCBs. The transformer need not be removed from service while the sample is taken. The amount of dielectric fluid which may escape is drastically reduced over prior art techniques. The possibility of the dielectric fluid becoming contaminated with water or dirt is also reduced because the lid of the transformer is not removed. Furthermore, problems associated with resealing the lid are eliminated. Sampling can be performed in virtually any type of weather.

I claim:

1. A method for obtaining a fluid sample from an electrical transformer of the type having a top and a bottom joined by a continuous wall so as to form a sealed vessel, the continuous wall having an inner wall surface enclosing primary and secondary windings positioned above the transformer bottom and a dielectric fluid, and an outer wall surface supporting secondary bushings, including a neutral secondary bushing, comprising the following steps:

locating a position on the outer wall surface between the neutral secondary bushing and the transformer bottom, and below the primary and secondary windings;

forming a bore at the located position partially through the continuous wall so that a reduced thickness wall portion remains adjacent to the inner wall surface;

placing a self-tapping screw, having a drilling end, a threaded midsection with a relatively constant diameter, a driving end, and a head for sealing the bore, into the bore;

rotating the driving end of the screw to advance the drilling end through the rediced thickness wall portion and to penetrate the inner wall surface until the sealing means seals the bore; and counterrotating the driving end of the screw until the fluid exits the bore to obtain the sample.

2. The method of claim 1 wherein the position-locating step includes the step of measuring approximately two inches up from the transformer bottom so that the windings are not inadvertently contacted during the bore-forming and screw-rotating steps.

3. The method of claim 2, including the step of maintaining electrical power to the primary windings during the bore-forming and screw-rotating steps.

4. The method of claim 2, including the steps of rerotating the driving end of the screw to reseal the bore, and coating an adjacent portion of the transformer outer wall surface with a material to discourage counterrotation of the screw.

5. The method of claim 1, including the step of attaching a collecting means to the transformer prior to the bore-forming step, said collecting means being used to collect fluid passing through said bore.

* * * * *

UNITED STATES PATENT AND TRADEMARK OFFICE
CERTIFICATE OF CORRECTION

PATENT NO. : 4,715,236
DATED : December 29, 1987
INVENTOR(S) : Thomas E. Willert It is certified that error appears in the above—identified patent and that said Letters Patent is hereby corrected as shown below:

Claim 1, line 23, delete "rediced" and substitute therefor --reduced--.

Signed and Sealed this

Fourteenth Day of June, 1988

Attest:

DONALD J. QUIGG

*Attesting Officer*     *Commissioner of Patents and Trademarks*